United States Patent [19]

Arditty et al.

[11] 4,209,252
[45] Jun. 24, 1980

[54] OPTICAL PROBE ASSEMBLY FOR DETECTING THE POSITION OF AN OBJECT SURFACE AND METHOD

[76] Inventors: Herve J. Arditty, 9 Chemin Du Bas Des Ormes, 78160 Marly Le Roi, France; Matt Lehmann, 212 San Hill Cir., Menlo Park, Calif. 94025; Jorlin E. Moon, 127 Seale Ave., Palo Alto, Calif. 94301; Sherwyne R. Bakar, 20051 Edinburgh Dr., Saratoga, Calif. 95070

[21] Appl. No.: 921,447

[22] Filed: Jul. 3, 1978

[51] Int. Cl.² .................. G01C 3/08; G01B 9/00; A61B 3/10
[52] U.S. Cl. ............................. 356/4; 351/6; 356/124; 356/127; 356/377
[58] Field of Search ............... 356/4, 5, 124, 127, 356/373, 375, 376, 377, 380; 351/5, 6

[56] References Cited

U.S. PATENT DOCUMENTS

| | | |
|---|---|---|
| 3,016,464 | 1/1962 | Bailey . |
| 3,567,320 | 3/1971 | Chitayat ............................ 356/4 |
| 3,589,815 | 6/1971 | Hosterman ....................... 356/376 |
| 3,847,485 | 11/1974 | Zanoni ............................. 356/375 |
| 4,007,990 | 2/1977 | McDevitt, Jr. et al. ............ 351/6 |

Primary Examiner—S. C. Buczinski
Attorney, Agent, or Firm—Flehr, Hohbach, Test

[57] ABSTRACT

An optical probe assembly for detecting the position of an object surface, especially the position of a three-dimensional, curved surface such as a surface in a contact lens or the cornea of the eye, is disclosed herein. This assembly and its method of operation use a beam of light which is focused to a point and an arrangement for automatically causing this point to move or scan in a predetermined way relative to the object surface including reciprocally through the surface for causing light to be reflected back from the latter. During this scanning period, when the beam point is coincident with the object surface, the amount of light which is reflected back along the path of the incident beam is maximized and automatically detected. At the same time, the position of the beam point relative to a known reference is automatically monitored and in combination with the detected light is used for determining the position of the object surface relative to this reference.

14 Claims, 7 Drawing Figures

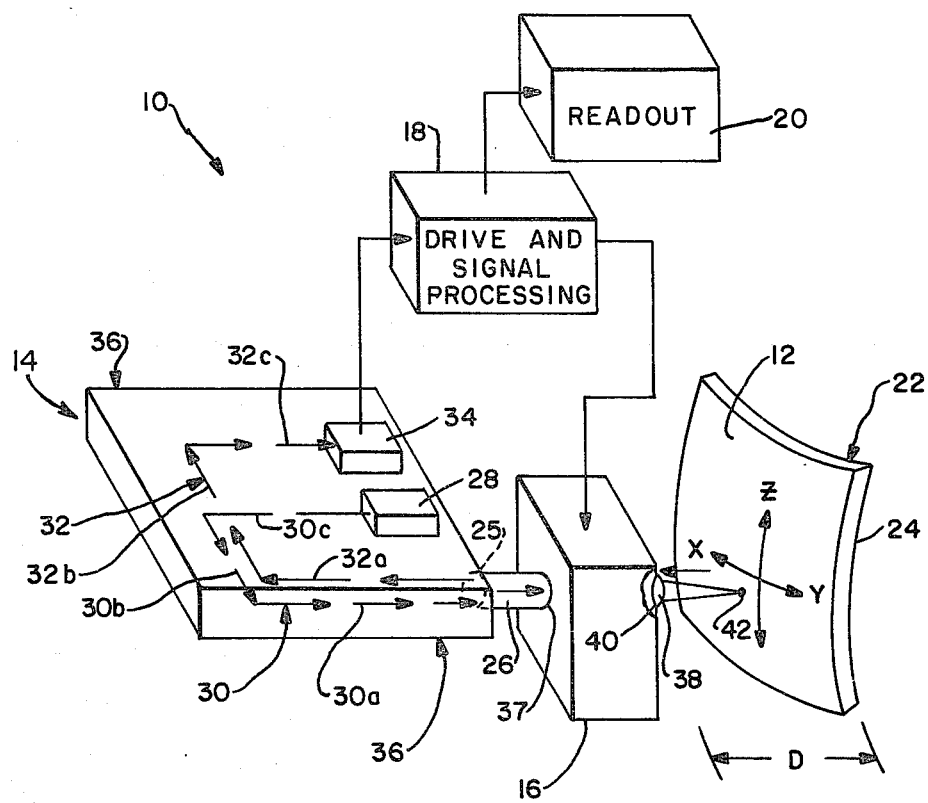
FIG.—1
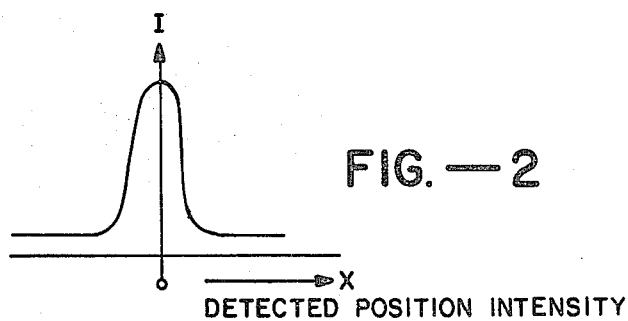
FIG.—2
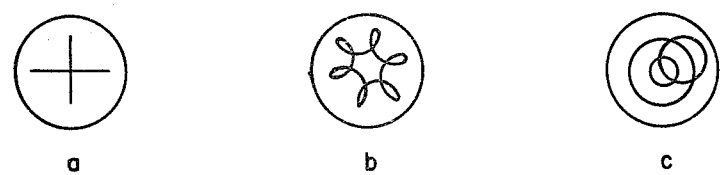
FIG.—6

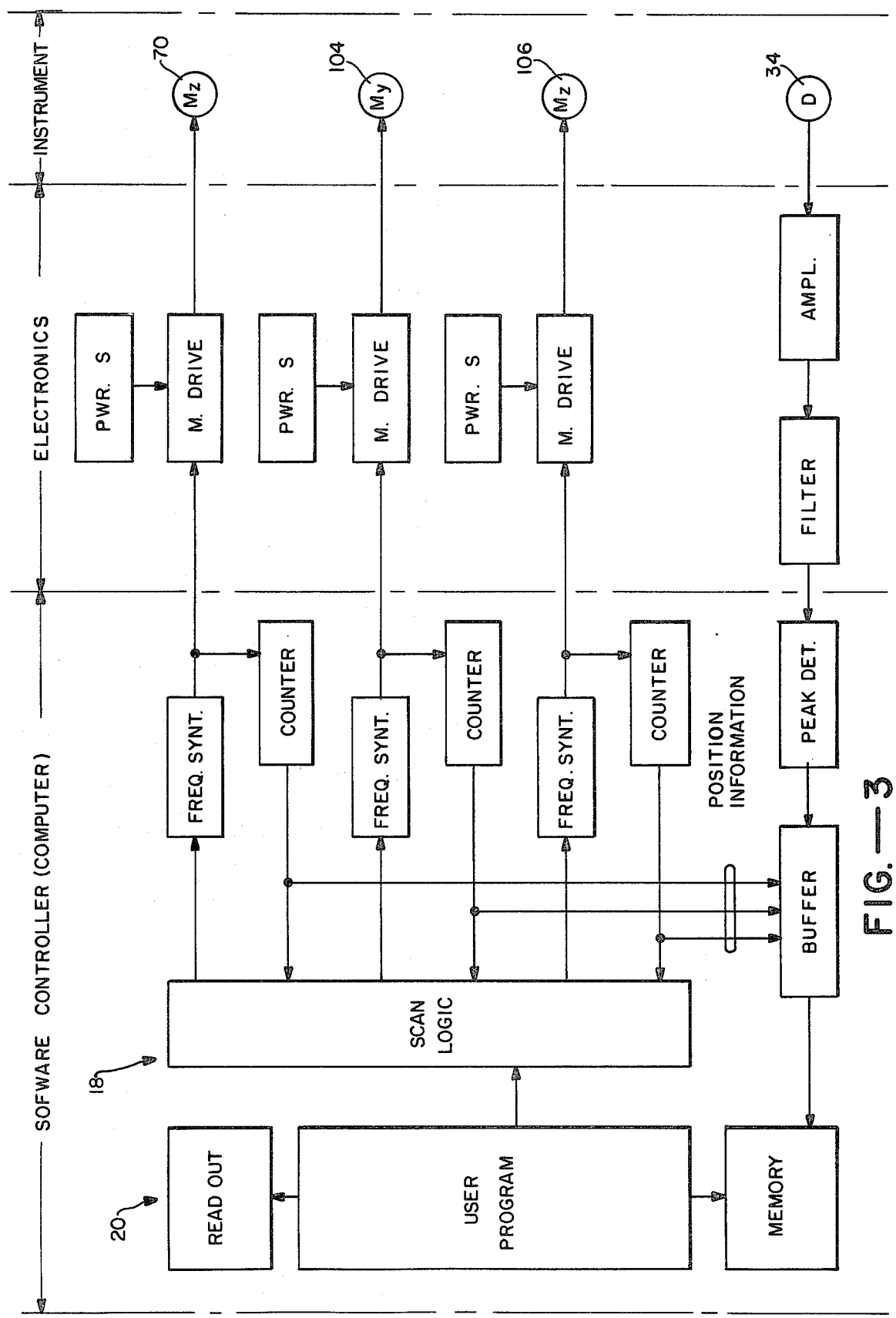
FIG.—3

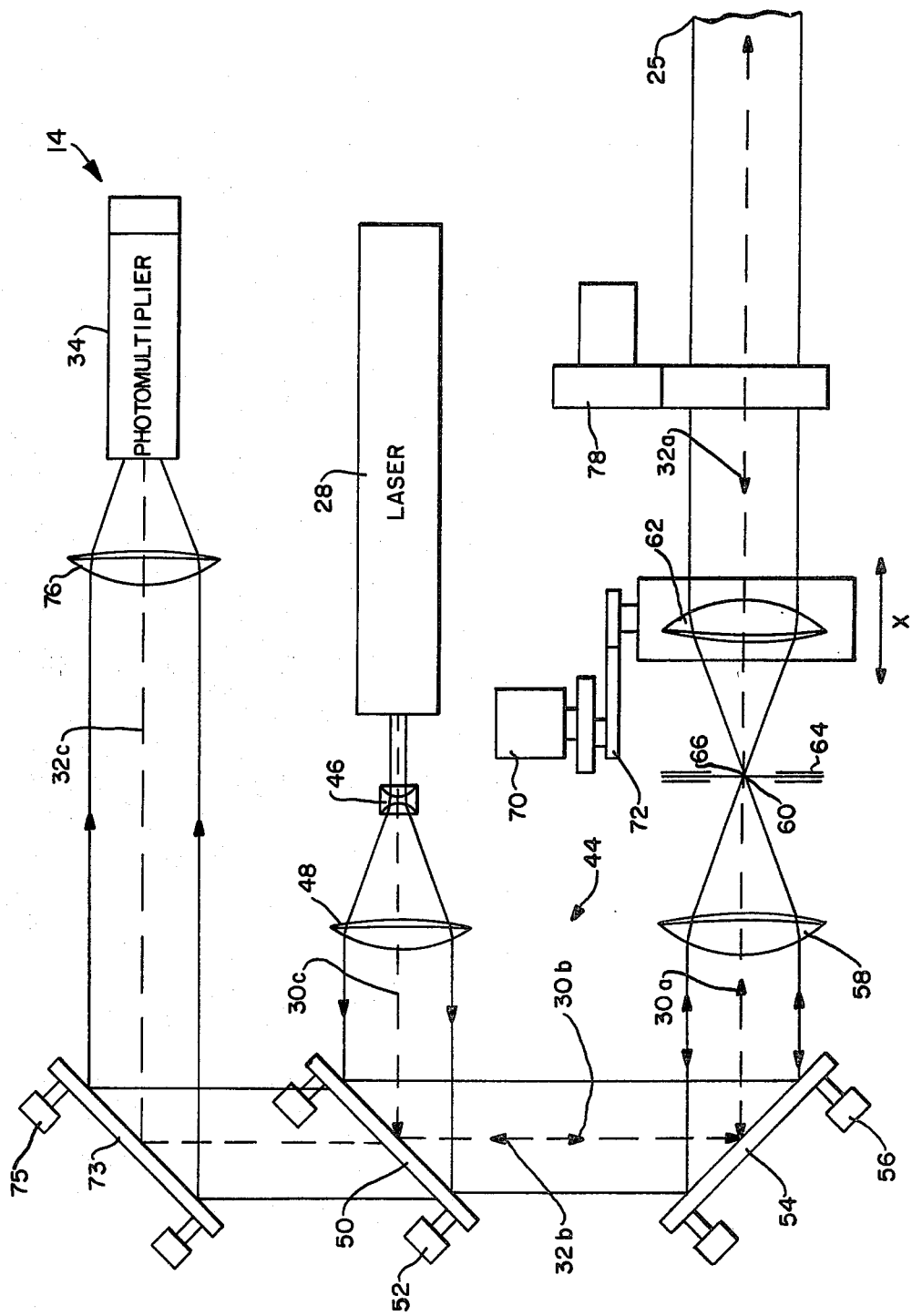
FIG.—4

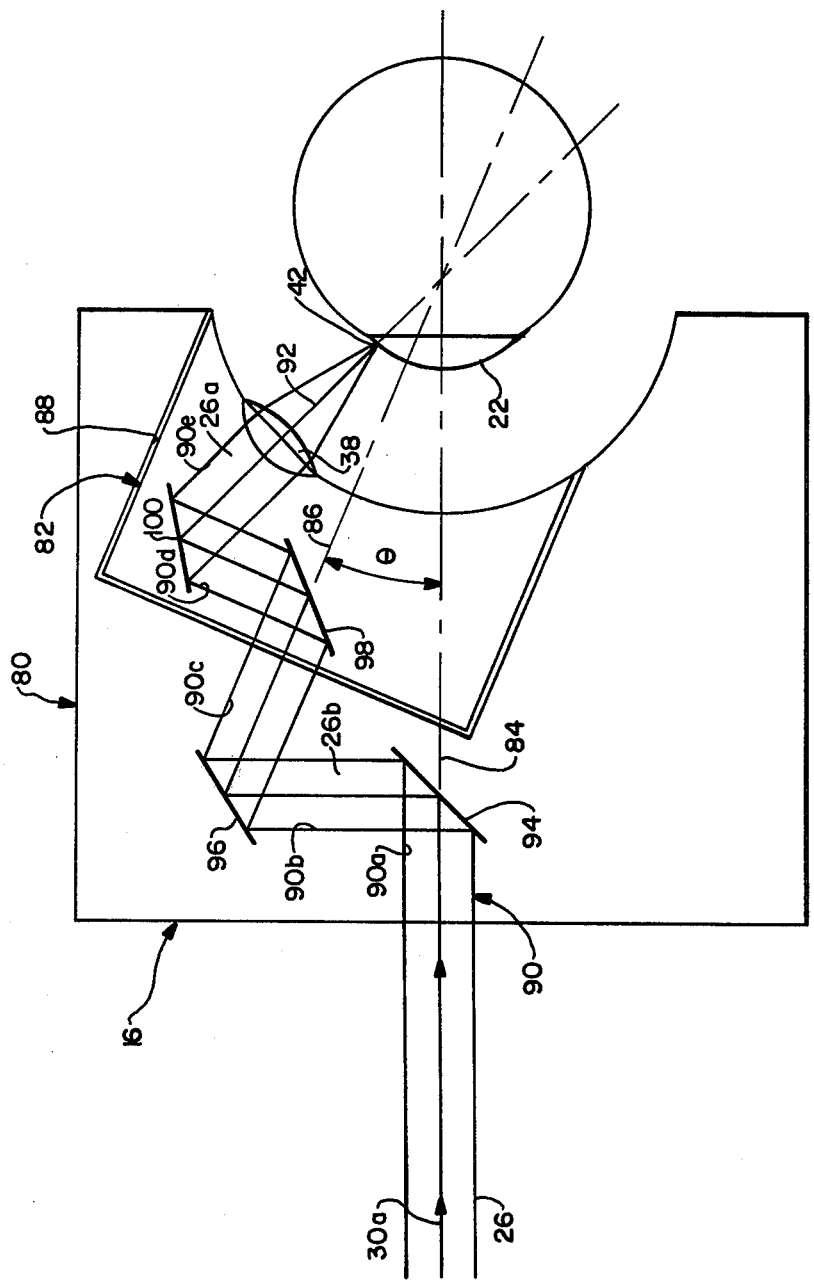
FIG.—5

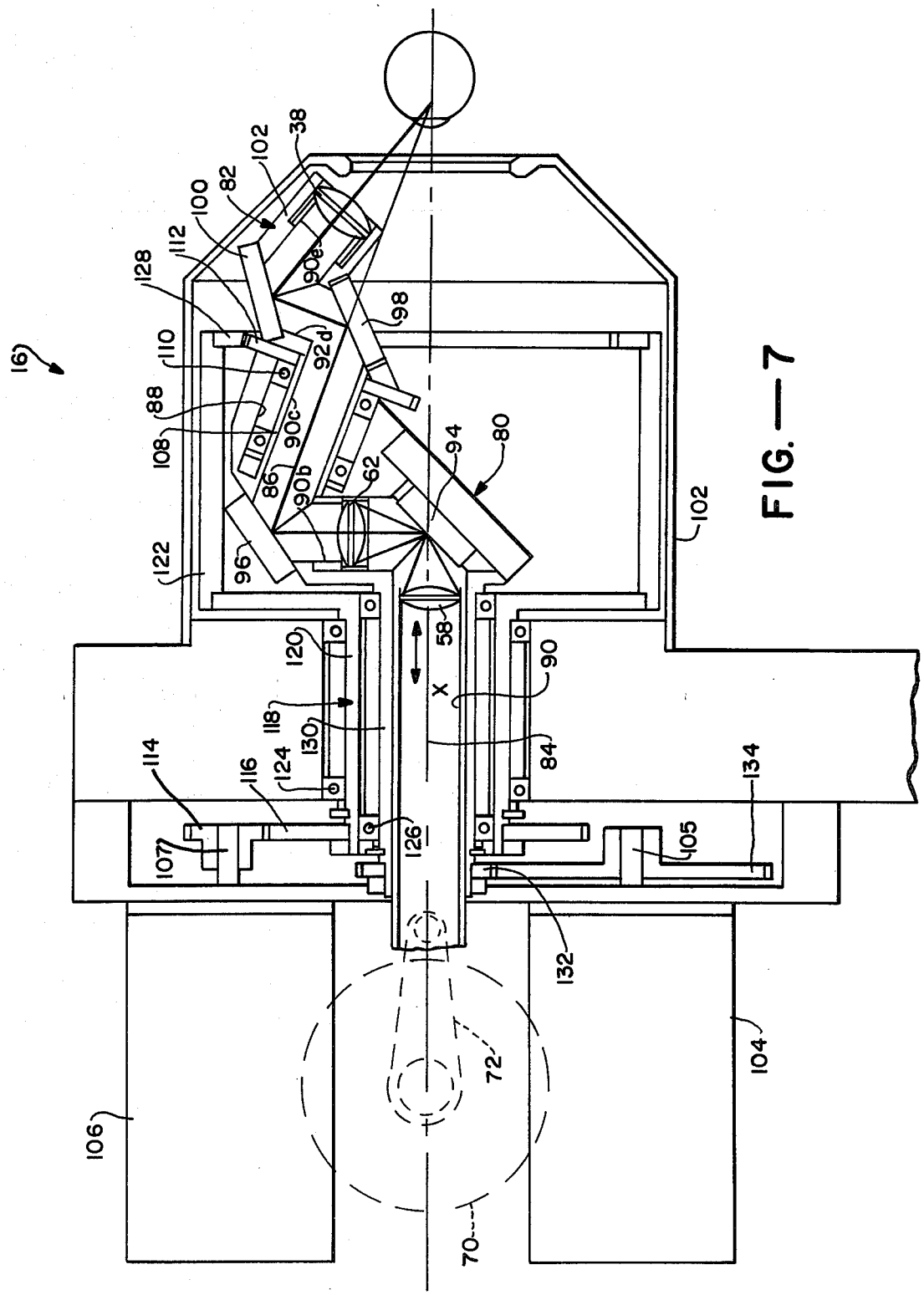
FIG.—7

OPTICAL PROBE ASSEMBLY FOR DETECTING THE POSITION OF AN OBJECT SURFACE AND METHOD

BACKGROUND OF THE INVENTION

The present invention relates generally to assemblies for and methods of detecting the position of an object surface and more particularly to an optical probe assembly and method for automatically detecting the position of an object surface relative to a known reference, especially the position of a three-dimensional, curved surface such as the outer surface (or surfaces) of a contact lens or even the cornea of an eye.

For many years, the hard plastic lens has been the mainstay of the contact lens industry. Its rigid structure allows it to be formed into many designs with precise optical dimensions and often the wearer of hard lenses will gain better vision than with conventional spectacles. In spite of the convenience and cosmetic appeal of the lenses, many patients experience comfort problems which have led to the development of the more comfortable hydrogel (soft) lens. In the past few years the growth of soft lenses has averaged over twenty percent per year, compared to about two percent per year for hard lenses, a trend which is expected to continue through 1980.

The major problem confronting the contact lens practitioner is that often he is not able to accurately measure many of the physical dimensions and optical properties of the lens. This is particularly true of soft lenses which are more prone to manufacturing errors and, because of their flexibility, are difficult to inspect. Parameters of hard lenses, on the other hand, can be more quantitatively examined. However, several important parameters of each type of lens cannot be dimensionally verified, and these are often critical to the fit and comfort of the lens. This causes the practitioner considerable frustration in fitting new patients as well as in ordering a duplicate lens for patients who are accustomed to the fit of specific lenses. A slight deviation in one or more of the lense parameters is enough to cause patient eye irritation and/or discomfort. Without the equipment to accurately measure the lens, the practitioner often orders new lenses of different specifications when a prescription change is not actually needed. These problems have created an urgent need within the industry for a more complete and accurate inspection of contact lenses which can be made by lens laboratories as well as in the practitioner's office.

As will be seen hereinafter, the present invention is directed to an assembly and method for detecting the position of an object surface, especially the three dimensional surface or surfaces of a contact lens, utilizing a beam of light. In this regard, the prior art discloses a number of ways in which a beam of light interacts with the surface of an object in order to obtain certain information regarding the latter. This prior art includes the following United States Patents:

| U.S. Pat. No. | Inventor |
| --- | --- |
| 2,466,015 | Ewing |
| 3,589,815 | Hosterman |
| 3,782,827 | Nisenson et al |
| 3,794,429 | Coeniger |
| 3,822,096 | Wilms et al |
| 3,892,494 | Baker et al |

-continued

| U.S. Pat. No. | Inventor |
| --- | --- |
| 3,988,068 | Sprague |
| 3,994,589 | Nodwell et al |

Of these references, the most pertinent to the present invention appears to be the Ewing patent which is directed to a manually operated apparatus for locating reflecting surfaces and for measuring the curvatures thereof. While an apparatus of this general type is indeed capable of measuring the curvature of a surface, it is inherently limited by its manual method of operation to rather imprecise measurements and cannot be reliably used in measuring the surface curvatures of a contact lens or the like. On the other hand, as will be seen hereinafter, the automated assembly of the present invention and its method of operation, which are significantly different than the assemblies and methods disclosed in the above recited patents including Ewing, provide sufficiently precise and reliable measurements of the position of an object surface relative to a known reference for enabling it to be used in measuring the curvatures of a contact lens or even the cornea of an eye. Moreover, as will also be seen, the overall assembly of the present invention is uncomplicated in design, relatively economical to provide, and readily adaptable for different uses, especially its optical probe and scanning mechanism.

OBJECTS AND SUMMARY OF THE INVENTION

One object of the present invention is to provide an automated assembly for determining the position of an object surface relative to a known reference utilizing a beam of light as the only means of contact with the surface being measured.

Another object of the present invention is to provide an assembly which is especially suitable for measuring a three dimensional, curved surface such as the outer surface (or surfaces) of a contact lens or the cornea of an eye.

Still another object of the present invention is to provide a reliable assembly of the last mentioned type which is uncomplicated in design, economical to provide and readily adaptable for different uses.

Yet another object of the present invention is to provide a separate and distinct optical probe which comprises part of the last mentioned assembly and which is responsible for providing a beam of light of predetermined cross sectional configuration along its length and for detecting light reflected back by the surface being measured along a path including the incident beam.

Still another object of the present invention is to provide an optical probe of the last-mentioned type which prevents the detection of light which is reflected back from the object surface along paths other than the incident beam path.

Yet another object of the present invention is to provide an optical probe which is independent of the rest of the overall assembly to the extent that it will function in the manner described regardless of the object surface being measured or the way in which the beam of light is optically moved to scan the object surface.

Still another object of the present invention is to provide an optical probe which minimizes optical noise caused by internal reflection.

Yet another object of the present invention is to provide an optical probe which is compact in design by virtue of its utilization of a folded light beam, but which provides rapid and reliable alignment of this folded light beam.

Still another object of the present invention is to provide a particular arrangement for scanning the beam of light relative to the object surface being measured, particularly an arrangement which is especially suitable for scanning a three dimensional, curved surface such as the surface or surfaces of a contact lens or even the cornea of an eye.

Yet another object of the present invention is to provide a scanning arrangement which is versatile in use so that the beam can be easily moved in a number of different ways within a three dimensional coordinate system.

A further object of the present invention is to provide a method of measuring the position of an object surface utilizing the assembly recited above.

As will be described in more detail hereinafter, the assembly and method for determining the position of an object surface relative to a known reference utilizes a beam of light of predetermined cross sectional configuration along its length. This beam of light is directed along a beam path at least a segment of which extends along a straight line adapted for alignment with and to impinge on the object surface being measured. A focusing lens is fixedly located within this segment in front of the object surface and has a focal point located on the axis of the path between the lens and object surface. In this way, the light beam passing through the lense converges to a point which is coincident with the focal point of the lense and which is provided for scanning the object surface.

This beam point just described is automatically caused to move in a predetermined way relative to the object surface and reference. This movement includes reciprocating movements along the axis of the straight line path segment sufficient to cause the beam point to cross through the object surface such that the latter causes at least some of the light from the beam to be reflected back along a reflection path including at least a section of the incident beam when the beam point is coincident with the object surface. At the same time, two signals are produced, a scanning signal which at any given instant is indicative of the position of the beam point relative to the known reference at that instant and a detection signal in response to the detection of light reflected back from the object surface along the path or path signal of the incident beam. These two signals are used for determining the position of the object surface relative to the known reference.

A more detailed discussion of this assembly and method will be provided hereinafter. Moreover, the particular ways in which the assembly and method of the present invention achieve the various objects set forth above will become apparent then.

BRIEF DESCRIPTION OF THE DRAWINGS

FIG. 1 is a perspective view of an overall assembly which is constructed in accordance with the present invention and which is provided for detecting the position of an object surface fixedly located relative to a known reference.

FIG. 2 is a graphic illustration of position versus detected light intensity resulting from operation of the assembly illustrated in FIG. 1.

FIG. 3 is a block diagram illustrating the operation of a part of the assembly illustrated in FIG. 1.

FIG. 4 is a schematic illustration of an optical probe comprising part of the assembly of FIG. 1.

FIG. 5 is a schematic illustration of one part of a scanning arrangement comprising a part of the assembly of FIG. 1.

FIGS. 6a, 6b and 6c diagrammatically illustrate three scans of an object surface by the arrangement illustrated in FIG. 5.

FIG. 7 is an elevational view, partially in section, of an actual scanning arrangement comprising part of the assembly of FIG. 1 and incorporating the principles illustrated FIG. 5.

DETAILED DESCRIPTION AND PREFERRED EMBODIMENTS

Turning now to the drawings, wherein like components are designated by like reference numerals throughout the various figures, an overall assembly 10 which is constructed in accordance with the present invention and which is provided for detecting and measuring the position of an object surface generally indicated at 12, is specifically illustrated in FIG. 1. As will be discussed in more detail hereinafter, this assembly includes an optical probe arrangement 14, a light beam scanning arrangement 16 and a drive and signal processing arrangement 18 including a readout device 20 which together cooperate to detect and measure surface 12 relative to a known reference, as stated previously. As illustrated in FIG. 1, surface 12 comprises one face of an object 22 which itself is a segment of a sphere. In an actual and preferred embodiment of the present invention, object 22 is a contact lens having a number of surfaces including front surface 12 and a back surface 24. Moreover, assembly 10 in its actual and preferred embodiment is especially suitable for automatically and sytematically detecting and measuring these surfaces whether the object is a hard lens or a soft lens and whether or not the lens is supported in air, the patient's eye or in a solution such as Saline, the latter being generally required for soft lenses when not being worn. As a result, the contact lens can be accurately measured for purposes of inspection, duplication, verification or the like. In this regard, the detailed description of assembly 10 to follow will be provided as it relates to detecting and measuring the surfaces of a contact lens or other such three-dimensional, curved surface which is somewhat spherical in nature. However, it is to be understood that this assembly can be utilized to detect and measure any surface, within practical limits, including flat surfaces, possibly with some slight modifications to be discussed.

As stated previously, assembly 10 includes an optical probe arrangement 14 which serves three primary purposes. First, it provides at its output indicated at 25 a beam of light 26 of predetermined cross sectional configuration along its length, preferably a collimated beam of light along at least most of its length. Second, it provides conventional means 28, for example a conventional laser producing device, for producing beam 26 and cooperating means (to be discussed) for directing this beam along a predetermined beam path 30, at least a segment 30a of which extends along a straight line. In a preferred embodiment, as will be seen hereinafter, path 30 is actually made up of three straight line segments, segment 30a and segments 30b and 30c. The beam of light produced may be of any practical wave length within the electromagnetic radiation spectrum including both visible and invisible light such as infrared radiation, the latter being particularly appropriate when object 22 is opaque to visible light and an internal or back surface is to be measured. However, when assembly 10 is intended for use in measuring the surfaces of a contact lens while the latter is maintained in place in the eye of a patient, dark blue light would be preferred since this is the least distractive if it were available from an economical standpoint. On the other hand, if object 22 is the eye itself and it is desired to measure deeper than the front surface of the cornea, it may be necessary to use a multi-wavelength beam. In this case the various components making up arrangement 14 including the various focusing and collimating lenses and detector (to be discussed) would have to be selected to operate at this multi-wavelength. Moreover, problems of chromatic dispersion would have to be corrected which would be done in a well known way. It is to be understood that assembly 10 is not limited to the multi-wavelength light, blue light or light of any specific wavelength and that the term "light beam" is intended to refer to a beam of electromagnetic radiation which is of any wave length within practical limits and which is compatible with the object being measured. The particular wavelength will in most cases depend on the object being measured.

As will be discussed hereinafter, light beam 26 is used to detect the various surfaces making up object 22, specifically including those illustrated, that is, surfaces 12 and 24. In order to do this, beam 26 is directed on to these surfaces in a way which causes a portion thereof to be reflected back into arrangement 14. In addition to producing beam 26 and directing the latter along path 30, arrangement 14 serves to direct this reflected light along a reflection path 32 including at least a segment 32a coincident with path 30a. Reflection path 32 also includes a second straight line segment 32b which, in part, is coincident with path 30b and a third straight line segment 32c. As seen in FIG. 1, this overall reflection path leads to a detector 34 for detecting the reflected light. This detector, like the beam generator 28 may be of conventional design, specifically adapted to detect electromagnetic radiation at the operating wavelength or wavelengths of beam 26.

A more detailed description of the various components making up arrangement 14 thus far described will be provided hereinafter. For the moment, it should suffice to say that this arrangement includes an overall support housing 36 within which beam generator 28 and detector 34 are mounted along with the various means for directing beam 26 along path 30 and the reflected light along path 32. By maintaining these various components fixed relative to one another, the same collimated beam 26 is produced at output 25 regardless of the position of the overall housing. This provides portability to arrangement 14 and, in fact, to the entire surface detecting and measuring assembly, as will be seen.

As stated previously, assembly 10 also includes a beam scanning arrangement 16. While this arrangement will be discussed in more detail hereinafter, a brief description of its primary function at the present time will serve to more fully appreciate the present invention. As illustrated in FIG. 1, this arrangement is positioned in alignment with the output 25 of arrangement 14 so that it receives the incident segment of beam 26 at its input 37. A focusing lens 38 comprising part of scanning arrangement 16 is fixedly located within incident path segment 30a at the output 40 of the scanning arrangement and has a focal point located on the axis of the path segment a predetermined distance beyond output 40. In this way, as beam 26 is directed through lens 38 by scanning arrangement 16, the light beam converges to a point 42 coincident with the focal point of the lens.

Scanning arrangement 16 not only serves to produce this beam point but also for causing it to move in a predetermined way relative to object surface 12 (and 24) relative to a known reference. More specifically, as will be seen hereinafter, scanning arrangement 16 is adapted to move beam point 42 along a three dimensional, curved surface within the X, Y, Z coordinate system including surfaces 12 and 24. At the same time, scanning arrangement 16 or preferably arrangement 14 causes the beam point to move normal to and through the surfaces in a reciprocating fashion along the X coordinate. The specific path of reciprocating movement of beam point 42 is fixed and known as indicated at D. Whether beam point 42 is moved by arrangement 16 or arrangement 14, some light from beam 26 is usually reflected back into arrangement 14 through scanning arrangement 16 by the object surface or surfaces. While a portion of the light may be reflected back along reflection path 32, the amount reflected back along this path is increased each time beam point 42 is coincident with a particular surface of object 22. Moreover, as will be discussed hereinafter, if the incident section of beam 26 (hereinafter referred to as the incident beam) is normal to this surface, the amount of light reflected back along path 32 is maximized.

In order to actually determine the position of surface 12 or surface 22, drive and signal processing arrangement 18 is utilized. This arrangement which will be discussed in more detail with respect to FIG. 3 includes a power supply provided for driving motors comprising part of scanning arrangement 16 (and arrangement 14 in a preferred embodiment) which in turn cause beam point 42 to scan within the X,Y,Z coordinate system described above while at the same time producing continuous signals which at any given instant are indicative of the position of the beam point within the coordinate system relative to a known reference. A system of this type can be readily provided by those with ordinary skill in the art. At the same time, detector 34 produces a signal at each instant beam 42 is coincident with the surface to be detected. These detection signals are applied to the drive and signal processing arrangement which conventionally monitors these signals with the scanning signals for determining the exact position of beam point 42 relative to a known reference at the instant the beam point is coincident with the surface or surfaces being measured, thereby determining the position of the surface or surfaces relative to the known reference. This is carried out in an automatic fashion by virtue of the fact that beam point 42 is automatically caused to move in the way described while the detection and scanning signals are automatically produced and coordinated to provide a continuous readout at 20. This readout may be visual, permanent or both.

Having described arrangement 18 generally, attention is directed to FIG. 3 for a more detailed discussion thereof. However, as stated above, this arrangement in and by itself may be conventionally provided and hence will not be discussed in great detail. As stated above, this arrangement is provided for controlling the movement of beam 42 throughout the X, Y, Z coordinate system. At the same time it is responsive to detector 34 for locating the position of point 42 when it is coincident with the surface or surfaces being detected, thereby determining the position of the surface or surfaces within the same coordinate system. In order to accomplish this, a conventional computer program referred to as a "user program" is used and controls a scan logic arrangement which is an ensemble of predetermined criteria governing the scanning mechanism of points 42. As seen in FIG. 3, this logic is applied to the inputs of frequency synthesizers X, Y and Z. Based on its input from the scan logic, each synthesizer generates a pulse train at a predetermined frequency or rate to an associated motor drive which is a conventional electronic circuit energized by an associated power supply. Each motor drive is provided for driving an associated stepping motor with the appropriate wave form dictated by the generated pulses. These motors labeled $M_x$, $M_y$ and $M_z$ includes respective shafts which move in discrete steps (angular intervals) in response to its input wave form and, as will be discussed hereinafter, are provided for moving point 42 in the X, Y and Z direction. At the same time that each frequency synthesizer is applying pulses to its associated motor drive, the same pulses are being applied to an associated counter which is a software memory device capable of counting events, specifically pulses. The output from each counter is applied back into the scan logic and also to a detector line to be discussed below.

Arrangement 18 thus far described in FIG. 3 is provided for keeping track of exactly where point 42 is within the X, Y, Z coordinate system at any given time during its operation. However, in order to determine the position of the surface being detected within the same coordinate system, arrangement 18 includes means responsive to the signal output from detector 34. As seen in FIG. 3, the detector output signal is applied to an analog electronic amplifier where the signal is amplified and thereafter applied to a preprocessing noise filter. The output from this filter is applied to a peak detector which, from a hardware standpoint, provides analog to digital conversion and, from a software standpoint, the digitized wave form is analyzed and the peaks are identified and numbered. The output from the peak detector is applied to a buffer which is an intermediate memory register containing the position information related to the current peak from the output of the peak detector. Note that the output from each counter described above is also applied to the buffer.

The information from the buffer is applied to a memory which in conjunction with the computer (user) program coordinates all of the information necessary to locate the surface or surfaces being detected. More specifically, arrangement 18 knows the position of point 42 at any given time (by means of the frequency synthesizers, motor drives and counters in conjunction with the scan logic) and it knows exactly when the beam point is coincident with the surface being detected (by means of the amplifier, filter and peak detector). All of this information is coordinated through the buffer, memory and user program, thereby providing an output which can be readily calibrated to indicate the position of the surface being detected at readout 20.

The various components of arrangement 18 just discussed may be separated into two groups, the electronics and the software controller (computer). The electronics include the power supplies, motor drives as well as the filter and amplifier. The software controller includes the frequency synthesizers, counters, peak detector and buffer as well as the scan logic, user program and memory and also readout 20. It is to be understood that these various components in and by themselves are conventional and can be readily provided by those with skill in the art in view of and based on the teachings herein.

Having described assembly 10 and its method of operation generally, attention is specifically directed to FIG. 4 for a more detailed discussion of optical probe arrangement 14. As illustrated in this figure, beam generator 28 which comprises part of the arrangement is illustrated as a laser which may be of any conventional type depending upon the wavelength of beam 26. In an actual working embodiment, the laser may not be essential. As beam 26 passes out of laser 28 it is directed to output 25 by an overall beam directing network which is generally indicated at 44 in FIG. 4. This network is preferably of the folded type, that is, it preferably breaks beam path 30 into multiple segments, specifically segments 32a, 32b and 32c, as previously stated. This has several advantages. First it reduces the dimensions of the overall arrangement 14 which, in turn, lends to the portability of the latter. Second, any optical system like the one thus far described has to be aligned so that the optical axes of all the elements are superimposed with one another. With a folded configuration which utilizes mirrors for providing the various path segments, it is only necessary to adjust the angles of the mirrors to provide proper optical alignment without moving the other components, of course assuming that the other components are in proximate alignment. Moreover, as will be seen below, the mirrors can be provided with adjustable mounting means such as gimbal mounts which allow the mirrors to be angularly adjusted with relative ease.

As seen in FIG. 4, network 44 includes a beam expander 46 located in path 30c directly in front of laser 28 for expanding beam 26 as it first leaves the laser. This expanded light is collimated by means of lens 48 and thereafter directed along path 30b by means of adjustable mirror 50 which, as stated above, includes adjustable mounting means which are generally designated at 52. As will be discussed hereinafter, mirror 50 actually acts as a beam splitter. A second mirror 54 including adjustable mounting means 56 is positioned in path 30b for redirecting the light beam along incident path 30a towards output 25. After the beam is reflected off of mirror 54, it passes through a first focusing lens 58 which causes the beam to converge and thereafter diverge at its focal point generally indicated at 60. Another focusing lens 62 is located on path 30a downstream of lens 58 and also has its focal point at point 60. In this way, as the beam passes through lens 58, it converges to point 60 and is thereafter recollimated as it passes through lense 62. For reasons to be discussed hereinafter, a light blocking plate 64 is positioned across path 30a at point 60 and includes an opening 66 which is slightly larger than point 60 and surrounds the point so that the light beam passes therethrough.

As stated previously, light beam point 42 is reciprocated along the X axis and, as also stated, this may be accomplished by scanning arrangement 16 but is preferably provided by arrangement 14. One way for arrangement 14 to provide this reciprocating movement is by mounting previously described focusing lens 62 on a support 68 as illustrated in FIG. 4. This support is in turn mounted to a conventional drive mechanism including motor 70 and drive linkage 72 which cause support 68 to reciprocate at a predetermined frequency, for example 60 cycles per second, along the axis of path 30a an extent equal to the distance D referred to in FIG. 1. This in turn produces similar movement of the focal point along the X axis, as described above. In this regard, motor 70 is driven by means of power supply system comprising part of drive and signal processing arrangement 18 which, as stated, monitors the position of the motor relative to a known reference and hence beam point 42 relative to a known reference and produces a scanning signal indicative thereof.

There is a specific advantage in providing reciprocating movement of point 42 within arrangement 14, as just described. Specifically, this places the reciprocating lens further away from the object being measured which, as stated, may be a contact lens within the eye of a patient, than would be the case if for example output lens 38 comprising part of scanning arrangement 16 were utilized for the same purpose. However, it is to be understood that the same type of device including motor 70 and linkage 72 could be readily provided for reciprocating lense 38 or, for that matter, another lense within the overall assembly.

As stated previously with respect to FIG. 1, each time beam point 42 is coincident with the surface being measured, for example surface 12 or 24, a relatively large portion of beam 26 is reflected back along its reflection path 32a which, as stated, is coincident with path 30a and a part of path 30b. As particularly illustrated in FIG. 4, this reflected light first enters arrangement 14 through output 25 and thereafter passes through lens 62 where it converges to point 60 and thereby passes through opening 66. Thereafter, it diverges and is recollumated by means of lens 58. Previously described mirror 54 redirects the reflected light along path 32 where it passes through previously described mirror 50 which in this respect acts as a beam splitter allowing passage of the reflected beam but reflecting beam 26 as previously described. A third mirror 73 which also includes gimbal mounts 75 redirects the reflected light along path 32c to the input of detector 28 which, as indicated, may be a photomultiplier or the like utilized for producing an electrical detection signal in response to the detection of reflected light. In this regard, a detecting lens 76 may be positioned in front of the detector for converging the reflector beam to the detector input.

As stated above, whenever beam point 42 is coincident with an object surface to be measured, light is reflected back along at least an initial segment of incident beam path 32a which in turn causes the reflected light to converge and diverge at point 60 in the same manner as originating beam 26. It should be apparent, however, that light from beam 26 may also be reflected back into arrangement 14 through output 25 when beam point 42 is either in front of the object surface to be measured or behind it, as stated previously. However, in this case most of the reflected light is not reflected back along a path coincident with the incident beam. Therefore as that reflected light passes through lense 62 its point of convergence is not aligned with opening 66 and hence most of this light does not pass plate 64 and never reaches detector 34. This is best illustrated in FIG. 2 which illustrates light intensity as seen by detector 34 Y-axis) versus the position of beam point 42 (X-axis) where the origin along the X-axis represents the position of point 42 when the latter is coincident with surface 12 or 24 along the Y axis. Note that detector 34 sees relatively little light when the beam point is in front of the surface being measured and very little light when the beam point is behind the surface. This is because at those times plate 64 prevents most of the reflected light which is light not coincident with path 32a from reaching the detector. However, when the beam point is on the surface being measured, the amount of light impinging on detector 34 is quite high.

In order to provide a more accurate reading by detector 34, it may be necessary to eliminate light which is reflected back towards the detector by the internal components making up arrangement 14 such as lens 58. One way to accomplish this is by providing network 44 with a device 78 mounted within the arrangement housing, preferably in path 30a (and 32a) just in front of the otherwise last component making up network 44, that is, lense 62. This device would be used to chop reflected light at a predetermined frequency as the light passes back along reflection path 32a. In this way, the detector 34 could distinguish between this pulsated light which represents the light actually reflected from the object surface and the internally reflected light which is not chopped and, hence, remains at a steady state level. Obviously, the beam chopper could be positioned at other locations along the reflection path but minimizes internal reflection noise by being positioned optically as far from the detector as possible.

Having described arrangement 14 in detail, attention is now directed to scanning arrangement 16 which is illustrated diagramatically in FIG. 5 in conjunction with an object 22 which in the figure is a contact lens located in position over the cornea of an eye. As seen in FIG. 5, this arrangement includes two cylindrical drums 80 and 82 which, as will be discussed hereinafter, are mounted for rotation about respective axes 84 and 86. The larger of these two drums, specifically drum 80, includes a forwardly facing pocket 88 which is adapted to receive the smaller drum 82 in the manner illustrated and the latter is adapted to support previously described lense 38 by suitable means. These two drums together define a continuous passage 90 which is comprised of five individual straight sections 90a, 90b, 90c, 90d and 90e. As seen in FIG. 5, passage 90a extends into drum 80 from its back end along rotation axis 84. Section 90b extends outward from section 90a towards one side of drum 80 and stops at rotation axis 86 which is at an acute angle $\theta$ with axis 84, specifically 22.5° in a preferred embodiment. Passage section 90c extends along axis 86 from section 90b into the back end of drum 82. Passage 90d extends outward from section 90c towards one side of this latter drum and section 90e extends along the axis of and directly behind lens 38.

For reasons to be discussed, lens 38 and contact lens 22 are positioned relative to one another such that the axis of the lens 38 generally designated at 92 (which coincides with the incident segment of beam 26) is coincident with the radius of curvature of contact lense 22 which may be considered spherical in shape. Moreover, as seen in FIG. 5, drum 80 is positioned such that its rotation axis 84 is coaxial with previously described path section 30a of light beam 26. In this way, the light beam enters passage 90a from output 25 of arrangement 14. Scanning arrangement 16 includes mirrors 94, 96, 98 and 100 which are respectively located at the junctures of path sections 90a to 90e for directing beam 26 through passage 90 and into the backside of lense 38 where the beam is converged to point 92, as described previously.

With drums 80 and 82 in the positions shown in FIG. 5 relative to contact lense 22 and light beam 26, both drums are caused to rotate about their respective axes in a predetermined way by means to be described hereinafter. As drum 82 rotates about its axis 86, it should be apparent that lens 38 and one section of beam 26, specifically section 26a directed along passage sections 90d and 90e and beam point 42 are caused to rotate about axis 86 while mirror 98 maintains this beam section in alignment with the rest of the beam. In addition, when the larger drum 80 is rotated about its axis 84, this causes the entire smaller drum 82 including beam section 26a, beam point 42 and lense 38 to rotate about the same axis. At the same time, section 26b of beam 26 which extends along passages 90b and 90c is also caused to rotate about axis 84 while mirror 94 maintains this section and hence both beam sections in optical alignment with incoming beam 26.

From the foregoing, several aspects of scanning arrangement 16 thus far described should be noted. For example, by synchronizing the rotation of both drums in predetermined ways, beam point 42 can be moved in any predetermined way to any point along the segment of a sphere within the X,Y,Z coordinate system which, in reality, is a radial ordinate system. Examples of this type of movement are illustrated in FIG. 6. For example, FIG. 6a shows beam point 42 moving only in two intersecting planes normal to one another which can be accomplished by moving the larger and smaller drums at a 2:1 ratio relative to one another. FIG. b illustrates the beam point moving in a raster type scan and FIG. 6c illustrates the beam point moving along a number of different circles. Obviously, other types of scanning movements could be provided.

Another aspect of scanning arrangement thus far described relates to the fact that the distance between lens 38 and object 22 remains substantially constant regardless of where the lense is within its scanning field, of course discounting reciprocating movement of part 42. This allows the reciprocating movement of the beam point along the X coordinate (which is coincidental with axis 92) to be very small while at the same time assuring that point 42 will move back and forth across the surface or surfaces being measured. Still another advantageous aspect of this scanning arrangement is that axis 92 remains substantially normal to the surface being measured since this axis is always substantially coincident with the radius of curvature of object 22. This maximizes the amount of light which is reflected back coincident with the incident beam when beam point 42 is coincident with the measuring surface. As a result, a smaller aperture lens 38 may be used which is important since the lense has to be operated very close to the object and therefore very close to the eye, for example, as close as a tenth of a millimeter. In this regard, it should be apparent that reciprocating movement of lense 38 for producing the corresponding reciprocating movement of beam point 42 would present a safety problem in this particular situation. Hence, in this case it is preferable to provide the reciprocating movement at a location upstream of lense 38, specifically within arrangement 14 as described previously. However, it should be understood that the means for providing this reciprocating movement described previously could comprise part of the scanning arrangement and, in fact, could be located within one of the rotating drums. drums.

Having described scanning arrangement 16 diagramatically, attention is now directed to FIG. 7 which illustrates an actual working embodiment of this scanning arrangement. As seen in this figure, both drums 80 and 82 are located within an overall housing 102 which supports a drive motor 104 including a drive shaft 105 and motor 106 utilizing drive shaft 107 utilized for rotating the drums in the manner described. In this actual working embodiment, each motor is an electrical stepping motor which is powered by means of a power supply described previously with respect to FIG. 3 and which is positionally monitored in the manner described for producing the previously described scanning signals. The mechanisms for coupling these motors to their respective drums will be discussed below.

As seen in FIG. 7, drum 82 includes a rearwardly extending cylindrical section 108 which is concentric with and defines previously described passage section 90c. Section 108 is supported for rotation about axis 86 within previously described pocket 88 in drum 80 by means of bearings 110. Rotating section 108 carries with it the rest of drum 82 as well as lense 38 and a disc gear 112 fixedly mounted around its outer surface. This gear comprises part of an overall network of gears for coupling drive shaft 107 of motor 106 with drum 82 for rotating the latter. This gear network also includes a gear 114 mounted to and around drive shaft 107 for rotation therewith. This latter gear is coupled to a disc gear 116 fixedly mounted around the back end of a coupling cylinder 118 having a reduced back section 120 and an enlarged front section 122. This coupling cylinder is mounted for rotation between motor bearings 124 located between reduced section 120 and housing 102 and inner bearings 126 located between the reduced section and a section of drum 80 to be described below. As seen in FIG. 7, the forwardmost free end of enlarged section 122 includes gear teeth 128 which are designed to engage and drive previously described gear 112. In this way, it can be seen that as motor 106 drives its shaft 107, gear 114 is rotated which, in turn, causes coupling cylinder 118 to rotate about previously described axis 84. This rotational movement is translated to gear 112 which causes drum 82 to rotate about axis 86.

Turning now to the larger drum 80, it can be seen that this drum includes a rearward cylindrical section 130 concentric with axis 84 and supported for rotation by bearings 126. The gear mechanism used for coupling driveshaft 105 of motor 104 is less complicated than the gear mechanism described above. In fact, the entire gear mechanism used to drive drum 80 in the embodiment illustrated consists of a first disc gear 132 fixedly mounted to the back end of cylindrical section 30 and the second disc gear 134 fixedly mounted to drive shaft 105. These two gears mesh with one another so as to drive drum 80 in the manner described.

It should be obvious from the foregoing that the two motors 104 and 106 can be driven in many predetermined ways and at any predetermined speeds, of course within practical limits, for driving their associated drums and therefor causing previously described focal point 42 to move along the section of a sphere as defined by the previously recited radial coordinate system. It should be equally apparent that the position of the shaft of each motor can be continuously monitored relative to a reference and hence the beam point 42 can be continuously monitored within the radial coordinate system relative to that reference. Moreover, motor 70 (FIG. 4)

which is used to reciprocate lens 62 for causing similar movement of beam point 42 can also be monitored in the same way, thereby monitoring the position of the beam point along the reciprocating coordinate (the X axis) relative to a known reference. In this regard, while it is preferable to provide this reciprocating movement at a point located within arrangement 14 as stated, this particular movement could be provided within scanning arrangement 16 as also stated. In this latter case, the same motor 70 and coupling network 72 could be located within the scanning arrangement along with a pair of converging and diverging lenses similar to previously described lenses 58 and 62 and generally designated at 58' and 62'. While not shown, the second of these two lenses, specifically lense 62', would be supported for reciprocating movement by motor 70 in the manner described previously.

Finally, with respect to scanning arrangement 16, attention is specifically directed to a preferred embodiment of the gearing mechanisms. As seen in FIG. 7, if motor 106 is maintained in a de-energized state, then it does not drive drum 82, and coupling cylinder 118 including gear teeth 128 remains fixed relative to housing 102. However, if at the same time, motor 104 is energized for driving drum 80 about axis 84, drum 82 is also caused to rotate about this latter axis. Hence, since gear 112 is fixedly connected with drum 82, it is caused to engage gear teeth 128 as the smaller drum moves which, in turn, causes this latter drum to simultaneously rotate about its own axis 86. In a preferred embodiment of the present invention, the gear mechanisms of the two drums are designed such that there is a 2:1 ratio in movement between the two drums under the circumstances just described, that is, when motor 104 is operative for driving its drum while motor 106 remains inoperative. This 2:1 ratio results in the scanning pattern illustrated in FIG. 6a, that is, the planar pattern. Hence, to provide this particular pattern which is required under many circumstances, the operator needs merely to operate motor 104 while maintaining motor 106 inoperative.

What is claimed is:

1. An assembly for detecting the position of an object surface which is fixedly located relative to a known reference, said assembly comprising:
   (a) means for producing a beam of light of predetermined cross-sectional configuration along its length;
   (b) means for directing said beam along a predetermined beam path at least a segment of which extends along a straight-line adapted for alignment with and to impinge on said object surface;
   (c) a focusing lens fixedly located within said path segment in front of said surface and having a focal point located on the axis of said path segment therebetween, whereby said beam passing through said lens converges to a point coincident with said focal point;
   (d) scanning means for automatically causing said beam point to move in a predetermined way relative to said object surface and said reference for scanning said surface, said movement including a reciprocating movement along the axis of said path segment, said reciprocating movement being sufficient to cause said beam point to cross through said object surface, whereby said surface causes at least some of the light deforming said beam to be reflected back along a reflection path including at least a section of said beam path segment when said beam point is coincident with said surface, said scanning means producing scanning signals which together at any given instant are indicative of the position of said beam point relative to said reference at that instant, said scanning means including an arrangement for automatically moving said focusing lens and one section of said beam including said lens while maintaining said section in optical alignment with the rest of said beam so as to cause said beam point to move along one section of an imaginary sphere in a predetermined coordinate system relative to said object surface for detecting the position of a similarly shaped surface, said moving arrangement including
   (i) first means for rotating said focusing lens and a segment of said beam section including said lens about a first predetermined rotation axis while maintaining said beam segment in optical alignment with the rest of the beam section, and
   (ii) second means for rotating said beam segment and lens and the rest of said beam section about a second predetermined rotation axis while maintaining said beam segment in optical alignment with the rest of said beam section and while maintaining the entire beam section in optical alignment with the rest of said beam;
   (e) means for detecting said reflected light and producing a detection signal in response thereto; and
   (f) means connected with said detecting means and said scanning means and responsive to said signals for determining the position of said surface relative to such reference.

2. An assembly according to claim 1 including an arrangement for substantially preventing any light which initially forms part of said beam and which is reflected off of said surface but which is not coincident with said reflection path from reaching said detector.

3. An assembly according to claim 2 wherein said light preventing arrangement includes
   (a) an intermediate focusing lens located on said reflection path and having a focal point located on the axis of said reflection path between said intermediate lens and said detector, whereby said reflected light passing through said intermediate lens converges to a point coincident with said last mentioned focal point, and
   (b) light blocking means located on said reflection path in a plane through the focal point of said intermediate lens, said light blocking means including a through hole coincident with said last mentioned focal point and slightly larger than the reflected light converging thereat, whereby said converged light passes therethrough.

4. An assembly according to claim 3 including means located within said beam path for diverting said reflected light along a section of said reflection path separate from said beam path whereby said reflection path includes only a section of said beam path and wherein said intermediate focusing lens and said blocking means are located on said diverted reflection path.

5. An assembly according to claim 3 wherein said light preventing arrangement includes a second intermediate focusing lens located within said reflection path between the first-mentioned intermediate lens and said detector and having a focal point coincident with the focal point of said first-mentioned intermediate lens whereby to cause said reflected light to be collimated as the latter passes through said second intermediate lens from its focal point.

6. An assembly according to claim 5 wherein each of said intermediate lenses and said light blocking means are located on said reflection path including said beam path section whereby said light beam passing therethrough towards said object surface is first caused to converge to a point within said through-hole and then to diverge.

7. An assembly according to claim 1 including beam chopping means including means for intermittently passing through said reflected light at a predetermined point along said reflection path for causing said reflected light to pulsate.

8. An assembly according to claim 1 wherein said beam path includes a plurality of segments extending along distinct straight lines and mirror arrangements for optically interconnecting said segments, said arrangement including mirror surfaces and means for supporting said mirror surfaces in adjustably fixed positions relative to said beam path for optically aligning said path segments with one another.

9. An assembly according to claim 1 wherein said moving arrangement includes means for moving said lens in a reciprocating manner for causing said reciprocating movement of said beam point.

10. An assembly according to claim 1 wherein said scanning means includes a second separate arrangement for causing said reciprocating movement of said beam point without reciprocating said lens, said separate arrangement being located on said beam path between said beam producing means and said focusing lens.

11. An assembly according to claim 10 wherein said separate arrangement includes a pair of intermediate focusing lenses located within and aligned with said beam, said pair of lenses having focal points coincident with and between one another and means for reciprocating one of said pair of lenses along the axis of said path.

12. An assembly according to claim 1 wherein said first rotating means includes means for supporting said focusing lens and means for driving said support means, said supporting means and driving means being interconnected such that rotation of said focusing lens about said second rotation axis by said second rotating means while said first rotating means remains inoperative causes said focusing lens to rotate about said first rotation axis at a rate one-half its rotation rate about said second rotation axis.

13. In an assembly for detecting the position of a three-dimensional, curved surface, for example, the outer surface of a contact lens or the cornea of the eye, using a beam of light focused to a point by means of a focusing lens, an arrangement for causing said beam point to move in a predetermined way relative to said surface for scanning the latter with said beam, said arrangement comprising:

(a) first means for rotating said focusing lens and a first segment of said beam including said beam point about a first axis while maintaining said beam segment in optical alignment with the rest of said beam including a second adjacent segment thereof; and (b) second means for rotating said focusing lens and first beam segment including said beam point and said second beam segment about a second axis while maintaining said second beam segment in optical alignment with said first segment and the rest of said beam.

14. An assembly according to claim 13 wherein said first rotating means includes means for supporting said focusing lens and means for driving said support means, said supporting means and driving means being interconnected such that rotation of said focusing lens about said second rotation axis by said second rotating means while said first rotating means remains inoperative causes said focusing lens to rotate about said first rotation axis at a rate one-half that of its rotation rate about said second rotation axis.

* * * * *